United States Patent [19]
Karjalainen et al.

[11] Patent Number: 5,498,623
[45] Date of Patent: Mar. 12, 1996

[54] 4(5) SUBSTITUTED IMIDAZOLES AND THEIR PREPARATION AND USE

[75] Inventors: Arto J. Karjalainen, Oulu; Raimo E. Virtanen, Rusko; Arja L. Karjalainen; Maire M. Eloranta, both of Oulu; Jarmo S. Salonen, Turku; Hannu T. Sipila, Turku; Antti S. Haapalinna, Turku, all of Finland

[73] Assignee: Orion-yhtyma Oy, Espoo, Finland

[21] Appl. No.: 244,932

[22] PCT Filed: Dec. 18, 1992

[86] PCT No.: PCT/FI92/00349

§ 371 Date: Sep. 19, 1994

§ 102(e) Date: Sep. 19, 1994

[87] PCT Pub. No.: WO93/13074

PCT Pub. Date: Jul. 8, 1993

[30] Foreign Application Priority Data

Dec. 12, 1991 [GB] United Kingdom ............ 9127050

[51] Int. Cl.⁶ .................... C07D 233/54; A61K 31/415
[52] U.S. Cl. .................... 514/396; 514/397; 548/311.4; 548/343.5
[58] Field of Search ............... 548/311.4, 343.5; 514/396, 397

[56] References Cited

U.S. PATENT DOCUMENTS

| | | | |
|---|---|---|---|
| 3,740,417 | 6/1973 | Hess et al. | 548/311.4 |
| 3,927,018 | 12/1975 | Houlihan | 548/311.4 |
| 3,927,023 | 12/1975 | Brown et al. | 548/311.4 |
| 4,411,908 | 10/1983 | Chapleo et al. | 548/311.4 X |
| 4,510,149 | 4/1985 | Cozzi et al. | 514/341 |
| 4,588,738 | 5/1986 | Cozzi et al. | 514/399 |
| 4,966,973 | 10/1990 | Goto et al. | 548/311.4 X |
| 5,204,364 | 4/1993 | Carganico et al. | 514/399 |
| 5,310,930 | 5/1994 | Sevilla et al. | 548/311.4 |

FOREIGN PATENT DOCUMENTS

| | | | |
|---|---|---|---|
| 0310745 | 4/1989 | European Pat. Off. | 548/311.4 |
| 0310746 | 4/1989 | European Pat. Off. | 548/311.4 |
| 92-05171 | 4/1992 | WIPO | 548/311.4 |

Primary Examiner—Floyd D. Higel
Attorney, Agent, or Firm—Ronald J. Kubovcik

[57] ABSTRACT

The invention provides compounds of the formula

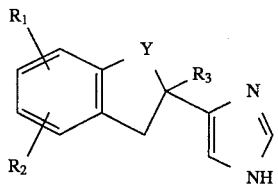

wherein
Y is —$CH_2$— or —CO—;
$R_1$ is F, Cl or OH; $R_2$ is H, F or Cl; and $R_3$ is H, $CH_3$ or $CH_2CH_3$, excluding 4-(5-chloro-2,3-dihydro-1H-inden-2-yl)-1H-imidazole and 4-(4-chloro-2,3-dihydro-1H-inden-2-yl)-1H-imidazole; and their non-toxic acid addition salts and mixtures thereof. Processes for the preparation of these compounds are described, as are pharmaceutical compositions comprising at least one of the compounds or its salt. The compounds and their non-toxic salts exhibit valuable pharmacological activity and are highly selective and long acting antagonists at $\alpha_2$-adrenoceptors. Their peroral bioavailability is good. The compounds are especially useful in the treatment of cognitive disorders.

25 Claims, 3 Drawing Sheets

4(5) SUBSTITUTED IMIDAZOLES AND THEIR PREPARATION AND USE

The present invention relates to novel 4(5)-substituted imidazole derivatives and their non-toxic salts, to their preparation, to pharmaceutical compositions containing them, and to their use.

The imidazole derivatives of this invention have the general formula:

(I)

wherein

Y is —$CH_2$— or —CO—

$R_1$ is F, Cl or OH; $R_2$ is H, F or Cl; and $R_3$ is H, $CH_3$ or $CH_2CH_3$ and pharmaceutically acceptable salts thereof, excluding 4-(5-chloro-2,3-dihydro- 1H-inden-2-yl)- 1H-imidazole and 4-(4-chloro-2,3-dihydro- 1H-inden-2-yl)-1H-imidazole.

The most preferable compounds according to the present invention are those wherein $R_1$ is F, $R_2$ is hydrogen or F, especially hydrogen. Also preferable are compounds, wherein $R_3$ is hydrogen or $CH_2CH_3$ and Y is —$CH_2$—. As specific examples of such preferred compounds are mentioned 4-(2-ethyl-5-fluoro-2,3-dihydro-1H-inden-2-yl)-1H-imidazole and 4-(5-fluoro-2,3-dihydro-1H-inden-2-yl)-1H-imidazole. These compounds are also valuable intermediates for the preparation of disubstituted indan-imidazole derivatives according to the invention.

The compounds of this invention are highly selective and long-acting antagonists of $\alpha_2$-adrenoceptors and they have good peroral bioavailability. The compounds are especially valuable in the treatment of cognitive disorders.

Valuable $\alpha_2$-adrenoceptor antagonists have been disclosed earlier e.g. in the European patent publications No. 183492, 247764 and 372954. PCT patent application No. 91/18886 discloses the use of some inden-imidazole derivatives, especially atipamezole, in the treatment of age-related memory impairment and other cognitive disorders. The compounds disclosed in these earlier patent applications, though some of them are very potent and selective $\alpha_2$-adrenoceptor antagonists, have usually a very short duration of action. This causes no problems when the compounds are used during clinical procedures. However, compounds with longer duration of action and good peroral bioavailability are necessary to obtain sufficient patient compliance. There are also indan-imidazole derivatives which have reported to have long duration of action e.g. those disclosed in EP 372954. However, such compounds are not so potent $\alpha_2$-adrenoceptor antagonists as the compounds of the present invention.

$\alpha$-Adrenoceptors can be divided on a pharmacological basis into two subclasses, viz $\alpha_1$-and $\alpha_2$-adrenoceptors (see e.g. Starke & Docherty, J. Cardiovasc. Pharmacol., I, Suppl. 1, 514–523, 1981). It is well established that while $\alpha_1$-adrenoceptors are located postsynaptically, $\alpha_2$-adrenoceptors are situated both at presynaptic nerve terminals and postsynaptically e.g. in vascular smooth muscle, platelets, pancreatic $\beta$-cells, fat cells and central nervous system.

The presynaptic $\alpha_2$-receptors modulate the release of noradrenalone by means of a negative feedback mechanism. Thus, if presynaptic $\alpha_2$-adrenoceptors are stimulated (under physiological conditions by noradrenaline) noradrenalone release in inhibited. Blockade of these receptors by an $\alpha_2$-antagonist, on the contrary, increases the release of noradrenaline, $\alpha_2$-Adrenoceptor antagonism at presynaptic $\alpha_2$-receptors can thus be expected to be of use in disease states which are believed to be connected with deficiency of noradrenaline available in the postsynaptic adrenoceptors. These diseases include e.g. endogeneous depression, age dependent memory impairment and other cognitive disorders, particularly Alzheimer's disease.

The best known pharmacodynamic effect mediated by postsynaptic $\alpha_2$-adrenoceptors is the contraction of vascular smooth muscle. Blockade of peripheral postsynaptic $\alpha_2$-adrenoceptors in blood vessels can thus be expected to dilate the vessel and lead to decrease in the blood pressure. $\alpha_2$-Blockers may thus be valuable as antihypertensive agents.

Glucose and lipid metabolism are also regulated by an inhibitory mechanism involving $\alpha_2$-adrenoceptors. An $\alpha_2$-antagonist may thus be of use in diabetes and obesity.

The following compounds of the invention were tested.

Table 1

No. Name 1. 4-(2-Ethyl-5-fluoro-2,3-dihydro-1H-inden-2-yl)-1H-imidazole
2. 4-(5-Fluoro-2,3-dihydro-2-methyl-1H-inden-2-yl)-1H-imidazole
3. 4-(2-Ethyl-5,6-difluoro-2,3-dihydro-1H-inden-2-yl)-1H-imidazole
4. 2-Ethyl-6-fluoro-2,3-dihydro-2-(1H-imidazol-4-yl)-1H-inden-1-one
5. 6-Chloro-2-ethyl-2,3-dihydro-2-(1H-imidazol-4-yl)-1H-inden-1-one
6. 4-(4-Fluoro-2,3-dihydro-1H-inden-2-yl)-1H-imidazole
7. 4-(5-Fluoro-2,3-dihydro-1H-inden-2-yl)-1H-imidazole
8. 2-Ethyl-2-(1H-imidazol-4-yl)-5-indanol The pharmacological activity of the compounds of the present invention was determined as follows:

1. $\alpha_2$-Antagonism in vitro $\alpha_2$-Antagonism was determined by means of isolated, electrically stimulated mouse vas deferens preparation (Marshall et al., Br. J. Pharmac. 62, 147, 151, 1978). In this model, $\alpha_2$-agonist (detomidine) blocks electrically stimulated muscular contractions and the effect of the $\alpha_2$-antagonist is seen by administering it prior to the agonist and by determining its $pA_2$ value. The known $\alpha_2$-antagonist atipamezole was used as a reference substance.

To obtain information also on the selectivity of the antagonist between $\alpha_1$- and $\alpha_2$-receptors, its ability to inhibit or stimulate $\alpha_1$-receptors was determined by means of isolated epididymal portion of rat vas deferens. The reference substances were now phenylephrine, a known $\alpha_1$-agonist, and prazosin, a known $\alpha_1$-antagonist. To determine $\alpha_1$-antagonism, muscular contraction was induced by phenylephrine and the $pA_2$ value of the studied compound was determined as above $\alpha_1$-Agonist effect is presented as the $pD_2$ value (negative logarithm of the molar concentration of the compound producing 50 percent of maximal contraction). Examples of the results are given in Table 2.

TABLE 2

| Compound | $\alpha_2$-Antagonism (pA$_2$ vs detomidine) mouse vas deferens | $\alpha_1$-Antagonism (pA$_2$ vs phenylephrine) rat was deferens | $\alpha_1$-Agonism (pD$_2$) rat was deferens |
| --- | --- | --- | --- |
| 1. | 8.2 | no effect | no effect |
| 2. | 7.3 | not measured | not measured |
| 3. | 7.2 | not measured | not measured |
| 4. | 5.9 | no effect | no effect |
| 5. | 6.6 | not measured | not measured |
| 6. | 8.1 | — | 6.5, full agonist |
| 7. | 8.0 | — | 5.5, partial agonist |
| 8. | 7.2 | not measured | not measured |
| atipamezole | 8.1 | 5.0 | no effect |

2. $\alpha_2$-Adrenoceptor antagonism in vivo

It is known that in the rat $\alpha_2$-agonists induce dilatation of the pupil (mydriasis) which effect is transmitted via postsynaptic $\alpha_2$-receptors in the central nervous system. In anaesthetized rat, a standard dose of an $\alpha_2$-agonist, detomidine, was administered intravenously. Thereafter increasing doses of the studied antagonists were injected intravenously and the reversal of detomidine-induced mydriasis was followed. The ED$_{50}$ value of the antagonist, i.e. the dose producing a 50 per cent reversal, was determined. Examples of the results of this test are presented in Table 3.

The duration of the $\alpha_2$-blocking action of the compounds was determined as follows: the antagonists were administered orally at equipotent doses to groups of 4 rats 1, 2, 4, 7 or 16 hours before induction of anaesthesia and challenge with cumulative i.v. dosing of detomidine. By calculating the percentage antagonism of the mydriatic effect of 0.1 mg/kg detomidine for each pretreatment group, a time-effect relationship was established. This in turn permitted the measurement of the time taken for the antagonist effect to fall by half. Results are shown in table 3.

The relative bioavailability of the antagonists when administered orally was evaluated by comparing the potency of their $\alpha_2$-blocking effect after peroral and parenteral administration. The antagonists were administered at equipotent doses (0.3 to 3 mg/kg) to groups of rats 1 hour before induction of anaesthesia and challenge with detomidine as described above in relation to the measurement of duration of action. The results are shown in Table 3.

TABLE 3

| Compound | $\alpha_2$-Antagonism ED$_{50}$ µg/kg iv) | t$_½$ of $\alpha_2$-antagonism | Peroral bioavailability |
| --- | --- | --- | --- |
| 1. | 15 | 3 | 81 |
| 4. | 300 | 6 | 89 |
| 7. | 10 | 7 | 80 |
| Atipamezole | 10 | 2 | 56 |

3. Effects on memory

The effects of atipamezole, MPV-1743 A III (compound 7) and MPV-1730 B III (compound 4) on learning and memory in linear arm maze task in rats were studied. The linear arm maze is a modified version of radial arm maze, which is a generally used memory test in rats. Atipamezole hydrochloride (0.3 mg/kg s.c.), MPV-1730 B III hydrochloride (3 mg/kg p.o.) and MPV-1743 A III hydrochloride (0.3 mg/kg s.c.) were dissolved in distilled water. Water was also used as control. All injections were made in a volume 1 ml/kg.

Apparatus: The maze was a wooden platform in a shape of two crosses one after another. The stem (starting arm) was 90 cm long and 12 cm wide. The five other arms (goal arms) were 50 cm long and 12 cm wide. Four goal arms were situated perpendicularly to the stem and to the fifth arm which located opposite to the stem. On either side of the stem and the arms were edges, 2.0 cm high. At the end of each goal arm a hole 1 cm deep and 3 cm in diameter, served as a food cup. The starting platform (20×20 cm) was separated from the stem by a quillotine door. The door was 12 cm high and 7 cm wide. The door frame was 20 cm high and 20 cm wide. The maze was elevated 31 cm above the floor, in a low-lighted test room which contained other objects as well as the test apparatus. The holes at the end of the goal arms were baited with three pellets of prize food (45 mg pellets Bio Serve Inc.).

Procedures: Two days prior to training, animals were placed on a food deprivation schedule that reduces their body weights to 90% of initial weights. During these days the rats were habituated to handling (three times/day), test room and prize food. On the second day they were also habituated to the unbaited maze: three to five animals from the same cage at the same time for ten minutes. On the third day the goal arms were baited, and the teaching trial, one rat at a time, was carried out. The rat received drug or distilled water and 60 minutes later it was placed in the starting platform. After ten seconds the door was opened and the rat was allowed to explore the maze until all the baits were found. The time to find all the baits and reentries made into already visited arms was recorded. This time every rate was allowed to stay in the maze at least for five minutes. On the next day the proper memory and learning testing began and continued for four days (testing days 1 to 4). Rats were given eight trials, two per day. Inter trial interval was 50 minutes. Drugs or distilled water were administered 30 minutes before the first trial of the day. Otherwise testing trials were identical to the teaching trial. All the observations were done blind so that test solutions were in coded flasks.

Statistical analysis: The results were expressed as mean time/trial/day (seconds) and mean errors/trial/day. The analysis of variance for the repeated measurements (ANOVA) was used to compare the drugs' and the testing days' effects on learning and memory.

Figure 1:
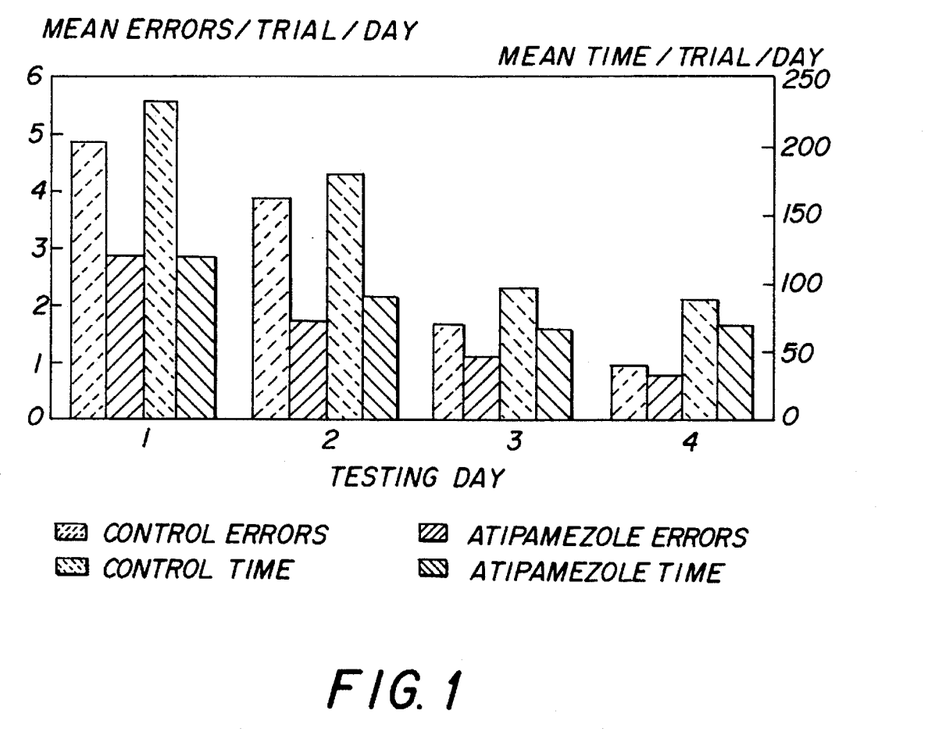
Figure 2:
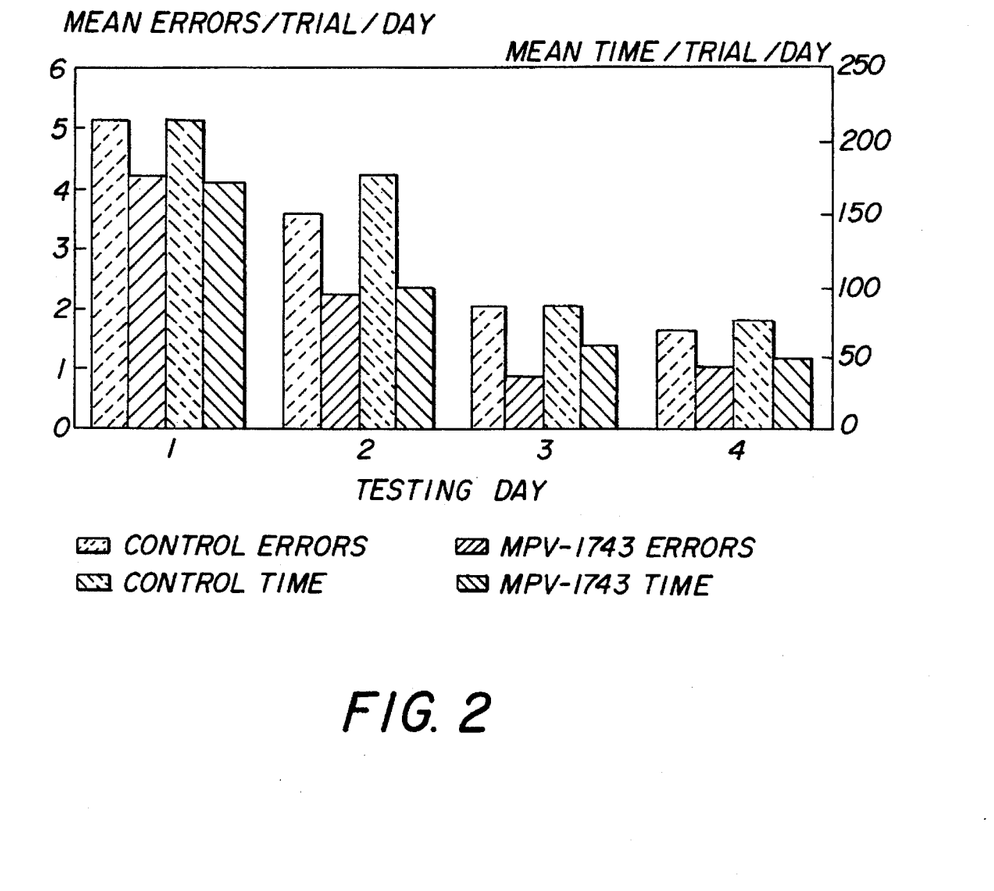
Figure 3:
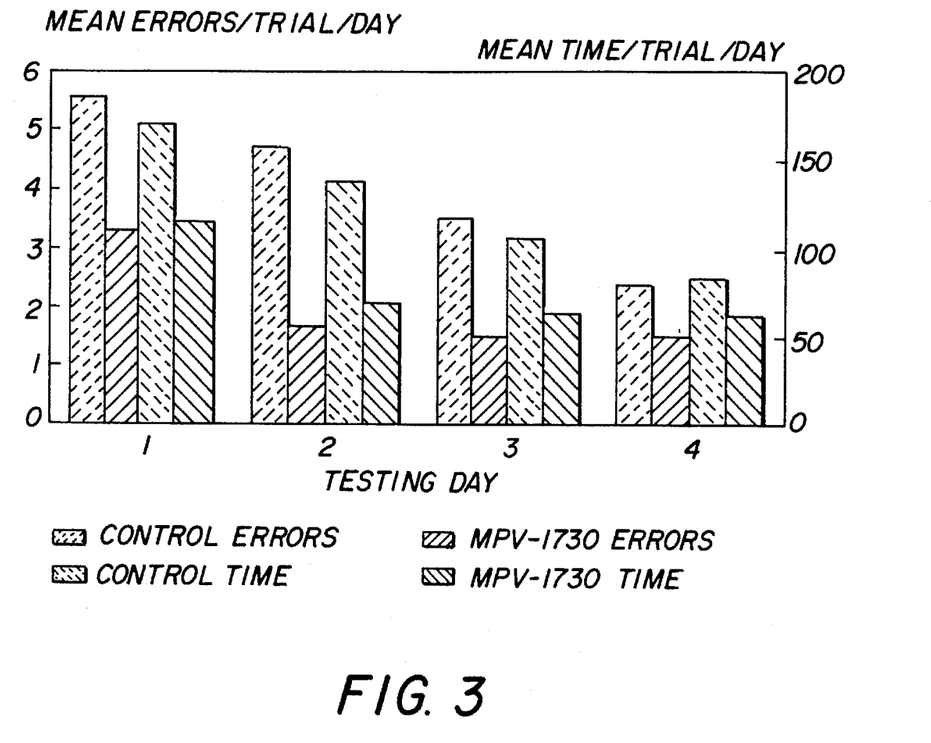

Results: The effects of atipamezole, MPV-1743 A III (=compound no. 7) and MPV-1730 B III (=compound no. 4) on learning and memory are presented in FIG. 1, FIG. 2 and FIG. 3 respectively. All tested drugs decreased number of errors i.e. reentrients into arms already visited during the same trial. This indicates an effect on working memory. All the drugs also decreased the time to solve the task. It is considered as an effect on learning and on speed to make correct choices. The number of errors and time decreased day to day also in the control group which indicates learning during testing. There were no any group x day-interaction, which means that the effect of the drugs did not depend on the testing day. These results suggest that atipamezole, MPV-1743 A III and MPV-1730 B III have learning and memory enhancing effects on adult rats.

The compounds of this invention react with organic and inorganic acids to form many pharmaceutically usable acid addition salts, as, for instance, chlorides, bromides, sulfates, nitrates, phosphates, sulfonates, formates, tartrates, maleates, citrates, benzoates, salicylates, ascorbates and the like. The salts have the same therapeutic activity as the base.

The compounds and their non-toxic, pharmaceutically acceptable acid addition salts may be administered orally, parenterally or intravenously. In the treatment of cognitive disorders the compounds are preferably administered orally at a daily dose of 0.1 to 10 mg/kg, preferably 0.2 to 1 mg/kg.

The pharmaceutical carriers which are typically employed with the compound of the invention may be solid or liquid and are generally selected with the planned manner of administration in mind. Choosing the auxiliary ingredients for the formulation is routine for those of ordinary skill in the art. It is evident that suitable solvents, gel forming ingredients, dispersion forming ingredients, colors etc are used in a normal way.

The acute toxicity ($LD_{50}$) using mice for the compounds of the invention is below 50 mg/kg (p.o.). For example, the $LD_{50}$ for 7-(4-(5-fluoro- 2,3-dihydro-1H-inden-2-yl)-1H-imidazole) is 100 mg/kg (p.o.).

The compounds of formula (I) can be prepared according to the following methods:

A compound of formula (II)

(II)

where $R_3$ is as defined above is nitrated with strong nitrating agent able to form the nitronium ion $+NO_2$, preferably with ureanitrate ($H_2NCONH_2 \times HNO_3$) in the presence of sulfuric acid, to give mainly the compound of formula (III)

(III)

but also a small amount of the compound of formula (IV), which compounds may be optionally separated (IV)

The nitro group of compounds (III) or (IV) is further reduced to the corresponding $NH_2$ group e.g. by catalytic hydrogenation using molecular hydrogen. Preferable catalysts are e.g. $PtO_2$ or Pd/C. The amino-substituted compounds so obtained can be separated from each other.

The amino substituted compounds (V)

and (VI)

are converted to their corresponding diazonium salts with nitrous acid which reagent is generated in the presence of the amine (V or VI) by the action of mineralic acid, preferably fluoroboric acid ($HBF_4$) on sodium nitrite at lowered temperature, preferably at about 0° C. The diazonium fluoroborate so formed can be termally decomposed to yield the fluoride (VII) or (VIII), boron trifluoride and nitrogen.

(VII)

(VIII)

wherein X is F.

The corresponding chlorosubstituted compounds can be formed by reacting the amine (V or VI) with hydrochloric acid and sodium nitrite at lowered temperature and then by reacting the diazonium group with a metal chloride, preferably copper(I) chloride, in concentrated hydrochloric acid at elevated temperature.

The monohalogenated compound of formula (VII)

(VII)

where X is F or Cl can further be nitrated by reaction with e.g. ureanitrate in sulfuric acid to give compound (IX)

(IX)

where the nitro group further can be replaced by a halogen via an amino group as described above to give a compound of formula (I) where $R_1$ and $R_2$ both are halogen.

Compounds of formula (I) where Y is CO, $R_1$ is F or Cl in the 6-position (X)

(X)

(X=F or Cl) can be achieved by nitrating a starting material of the formula XI (XI)

with e.g. ureanitrate in sulfuric acid and replacing the nitro group by an amino group which further is replaced by halogen according to the methods described above. Another halogen atom can further be introduced into the 4-position of the aromatic ring of compound (X) by nitration of the compound with e.g. ureanitrate in sulfuric acid, hydrogenation of the nitro group to an amino group, and finally replacing the amino group by a halogen according to the methods described above.

A compound of the formula XII can be prepared by reacting the compound of formula (V) e.g. with sodium nitrate in the presence of concentrated sulfuric acid at low temperature. The diazonium salt is then termally decomposed to yield the compound of formula (XII).

Further compounds of the invention may be prepared by analogy with the processes described in EP-A-183492.

In the examples below, where $^1$H and $^{13}$C NMR spectrum shifts are presented, the NMR spectra were obtained on a Bruker AC 300 P spectrometer using tetramethylsilane as the internal reference, from which the presented chemical shifts (δ, ppm) were measured downfield. The letters s, d, t, q and m are used to indicate a singlet, doublet, triplet, quartet or multiplet, respectively. In the same connection, the number of hydrogen atoms is also stated. The spectra of the compounds as bases were recorded in deuterium methanol or deuterium chloroform, while the values for compounds as hydrochlorides were determined in deuterium methanol. The mass spectra were recorded on a Kratos MS 80 RD Auto-console mass spectrometer.

EXAMPLE 1

4-(2ETHYL-5-FLUORO-2,3-DIHYDRO-1H-INDEN-2-YL)-1H-IMIDAZOLE

4-(2-Ethyl-2,3-dihydro-5-nitro-1H-inden-2-yl)-1H-imidazole 4-(2-Ethyl-2,3-dihydro-1H-inden-2-yl)-1H-imidazole (Karjalainen, A. J. et. al. U.S. Pat. No. 4,689,339; 3.00 g, 0.0141 mol) was added to 15 ml of concentrated sulphuric acid at 0° C. Ureanitrate (1.74 g. 0.0141 mol) was added in small portions at 0° C. After the reaction the solution was poured into ice water. The solution was made alkaline with sodium hydroxide and was extracted with ethyl acetate. The organic solution was dried over magnesium sulfate and evaporated. The yield of 4-(2-ethyl- 2,3-dihydro-5-nitro-1H-inden-2-yl)-1H-imidazole was 3.59 g (99%). The hydrochloride salt of the product was prepared in dry hydrogen chloride—ethyl acetate.

MS: 257 (22, M$^+$), 228 (100, M-CH$_2$CH$_3$), 182 (27, 228-NO$_2$)

The hydrochloride salt, $^1$H NMR (300 MHz, CD$_3$OD); δ0.82 (3H, t, J 7 Hz, CH$_2$CH$_3$), 1.97 (2H, q, J 7 Hz, CH$_2$CH$_3$), 3.31 and 3.41 (4H, AB q, J$_{AB}$ 17 HZ, the indan ring H$_2$-1 and H$_2$-3), 7.44 (1H, s, im-5), 7.46 (1H, d, H-7), 8.05 (1H, d, J 8 Hz, H-6), 8.10 (1H, s, H-4), 8.92 (1H, s, im-2)

4-(5-Amino-2-ethyl-2,3-dihydro-1H-inden-2-yl)-1H-imidazole

A solution of 4-(2-ethyl-2,3-dihydro-5-nitro-1H-inden-1-yl)-1H-imidazole (10.25 g, 0.03988 mol) in ethanol (150 ml) was hydrogenated over PtO$_2$ (1 g) at 3 atm pressure. When the uptake of hydrogen ceased the reaction mixture was filtered and evaporated to dryness to give 4-( 5-amino-2-ethyl-2,3-dihydro-1H-inden-2-yl)-1H-imidazole (8.2 g, 91%).

The product was purified by flash chromatography eluting with methylene chloride—methanol mixture (9.5:0.5). The hydrochloride salt of the product was made with dry hydrogen chloride in dry ethyl acetate—ether; mp. 145°–152° C.

MS: 227 (50, M$^+$), 212 (15, M-CH$_3$), 198 (100, M-CH$_2$CH$_3$)

Base. $^1$H NMR (300 MHz, CDCl$_3$); δ0.77 (3H, t, J 7 Hz, CH$_2$CH$_3$), 1.87 (2H, q, J 7 Hz, CH$_2$CH$_3$), 2.96 and 3.11 (2H, AB q, J$_{AB}$ 15 Hz, the indan ring H$_2$-1 or H$_2$-3), 2.98 and 3.13 (2H, AB q, J$_{AB}$ 16 Hz, the indan ring H$_2$-1 or H$_2$-3), 6.48 (1H, dd, $^3$J 8 Hz, $^4$J 2 Hz, H-6), 6.54 (1H, broad s, H- 4), 6.73 (1H, s, im-5), 6.95 (1H, d, $^3$J 8 Hz, H-7), 7.48 (1H, s, im-2)

The hydrochloride salt, $^{13}$C NMR (CD$_3$OD): δ9.82 (q), 33.35 (t), 44.15 (t), 44.53 (t), 48.92 (s), 117.34 (d), 120.47 (d), 122.64 (d), 127.12 (d), 130.63 (s), 135.67 (d), 140.69 (s), 143.71 (s), 144.97 (s)

4-(2-Ethyl-5-fluoro-2,3-dihydro-1H-inden-2-yl)-1H-imidazole

The flask containing fluoboric acid (48 wt. % solution in water, 25 ml) and 5.63 g (0.0248 mol) of 4-(5-amino-2-ethyl-2,3-dihydro-1H-inden- 2-yl)-1H-imidazole was placed in an ice-salt bath and cooled to 0° C. A solution of 2.6 g (0.0377 mol) of sodium nitrite in 5 ml of water was run in slowly while the temperature was kept at 0° C. After the addition the mixture was stirred for an hour at 0° C. and then for an hour at the room temperature. The reaction mixture was evaporated twice to dryness with toluene.

The thermal decomposition was carried out in the flask which was heated with an electric heating mantle. When the generation of white fumes of boron trifluoride ceased the heating was stopped.

The crude produce was dissolved in methanol, the solution was filtered and evaporated to dryness.

The product was purified by flash chromatography (the eluent methylene chloride—methanol 9.5:0.5). The hydrochloride salt of the product was prepared in ethyl acetate; mp. 152°–154° C.

MS: 230 (27, M$^+$), 201 (100, M-CH$_2$CH$_3$), 133 (14), 100 (15)

The hydrochloride salt, $^1$H NMR (300 MHz, CD$_3$OD): δ0.80 (3H, t, J 7 Hz, CH$_2$CH$_3$), 1.93 (2H, q, J 7 Hz, CH$_2$CH$_3$), about 3.11–3.30 (4H, m, the indan ring H$_2$-1 and H$_2$-3), 6.87 (1H, m, H-6), 6.96 (1H, dd, $^3$J$_{HF}$ 9 Hz, $^4$J$_{HH}$ 2 Hz, H-4), 7.18 (1H, dd, $^3$J$_{HH}$ 8 Hz, $^4$J$_{HF}$ 5 Hz, H-7), 7.37 (1H, d, J 1 Hz, im-5), 8.87 (1H, d, J 1 Hz, im-2)

The hydrochloric salt, $^{13}$C NMR (CD$_3$OD): δ9.87 (CH$_3$), 33.45 (CH$_2$CH$_3$), 43.99 (C-1), 44.74 ($^4$J$_{CCCCF}$ 2 Hz, C-3), 49.14 (C-2), 112.14 ($^2$J$_{CCF}$ 23 Hz, C-4), 114.55 ($^2$J$_{CCF}$ 23 Hz, C-6), 117.28 (im-5), 126.78 ($^3$J$_{CCCF}$ 9 Hz, C-7), 135.60 (im-2), 137.93 ($^4$J$_{CCCCF}$ 3 Hz, C-7a), 141.15 (im-4), 144.72 ($^3$J$_{CCCF}$ 8 Hz, C-3a), 163.75 (J$_{CF}$ 242 Hz, C-5)

EXAMPLE 2

4-(5-FLUORO-2,3-DIHYDRO-2-METHYL-1H-INDEN-2-YL)-1H-IMIDAZOLE

The procedure of Example 1 was also used to synthesize 4-(5-fluoro- 2,3-dihydro-2-methyl-1H-inden-2yl)-1H-imidazole and its intermediates from 4-(2,3-dihydro-2-methyl-1H-inden-2-yl)-1H-imidazole (Karjalainen, A. J. et. al. U.S. Pat. No. 4,689,339).

4-(2,3-Dihydro-2-methyl-5-nitro-1H-inden-2-yl)-1H-imidazole

MS: 243 (50, M$^+$), 228 (100, M-CH$_3$), 182 (30)

Base. $^1$H NMR (300 MHz, CDCl$_3$+CD$_3$OD): δ1.49 (3H, s, CH$_3$), 3.05 and 3.44 (4H, AB q, J$_{AB}$ 16 Hz, H$_2$-1 and H$_2$-3), 6.79 (1H, d, J 1 Hz, im-5), 7.36 (1H, d, J 9 Hz, H-7), 7.56 (1H, d, J 1 Hz, im-2), 8.04 (1H, d, J 9 Hz, H-6), 8.06 (1H, s, H-4)

4-(5-Amino-2,3-dihydro-2-methyl-1H-inden-2-yl)-1H-imidazole

MS: 213 (90, M$^+$), 198 (100, M-CH$_3$)

Base, $^1$H NMR (300 MHz, CDCl$_3$+CD$_3$OD): δ1.42 (3H, s, CH$_3$), 2.87 and 3.21 (2H, AB q, J$_{AB}$ 16 Hz, the indan ring H$_2$-1 or H$_2$-3), 2.86 and 3.18 (2H, AB q, J$_{AB}$ 15 Hz, the indan ring H$_2$-1 or H$_2$-3), 6.51 (1H, dd, $^3$J 8 Hz, $^4$J 2 Hz, H-6), 6.55 (1H, d, J 2 Hz, H-4), 6.74 (1H, d, J 1 Hz, im-5), 6.98 (1H, d, $^3$J 8 Hz, H-7), 7.52 (1H, J 1 Hz, im-2)

4-(5-Fluoro-2,3-dihydro-2-methyl-1H-inden-2-yl)-1H-imidazole

The hydrochloride salt: Mp. 188°–190° C.

MS: 216 (50, M$^+$), 201 (100, M-CH$_3$), 133 (18)

The hydrochloride salt, $^1$H NMR (300 MHz, CD$_3$OD): δ1.51 (3H, s, CH$_3$), 3.03–3.12 and 3.26–3.36 (4H, H$_2$-1 and H$_2$-3), 6.87–6.99 (2H, m, H-4 and H-6), 7.20 (1H, m, H-7), 7.38 (1H, s, im-5), 8.85 (1H, J 1 Hz, im-2)

EXAMPLE 3

2-ETHYL-2-(1H-IMIDAZOL-4-YL)-5-INDANOL

In a flask were place 0.76 g (0.00334 mol) of 4-(5-amino-2-ethyl- 2,3-dihydro-1H-inden-2-yl)-1H-imidazole, 2.7 ml of water and 0.76 ml of concentrated sulfuric acid. A solution was cooled to 0° C. and a solution of 0.47 g (0.00681 mol) of sodium nitrite in 1.52 ml of water was added so that the temperature during the diazotization was maintained at 0°–5° C. Stirring was continued for one hour at 0°–5° C.

While the diazotization was in progress, 2.28 ml of concentrated sulfuric acid was added to 1.9 ml of water in a flask and the solution was heated to boiling (160° C.). The solution from the diazotization was then added at such a rate that the acid mixture boiled. Boiling was continued for one hour. Water was poured into the cooled mixture. The pH value of the solution was adjusted to 7–8 and the precipitated impurities were filtered off. The water solution was extracted with several portions of ethyl acetate and the combined organic extractions were washed with water, dried with Na$_2$SO$_4$ and evaporated to dryness. The crude yield of the product was 0.6 g (79%). Purification was performed by flash chromatography (the eluent methylene chloride-methanol 9.5:0.5). The hydrochloride salt of the product was prepared in ethyl acetate; mp. 193°–196° C.

MS: 228 (38, M$^3$), 213 (12, M-CH$_3$), 199 (100, M-CH$_2$CH$_3$)

The hydrochloride salt, 1H NMR (300 MHz, CD3OD): δ0.79 (3H, t, J 7 Hz, CH2CH3), 1.91 (2H, q, J 7 Hz, CH2CH3), 3.06 and 3.15 (2H, AB q, JAB 15 Hz, the indan ring H2-1 or H2-3), 3.09 and 3.18 (2H, AB q, JAB 16 Hz, the indan ring H2-1 or H2-3), 6.57 (1H, dd, 3J 8 Hz, 4J 2 Hz, H-6), 6.65 (1H, d, 4J 2 Hz, H-4), 7.00 (1H, d, 3J 8 Hz, H-7), 7.31 (1H, d, J 1 Hz, im-5), 8.80 (1H, s, im-2)

EXAMPLE 4

2-ETHYL-6-FLUORO-2,3-DIHYDRO-2-(1H-IMIDAZOL-4-YL)-1H-INDEN-1-ONE

2-Ethyl-2,3-dihydro-2-(1H-imidazol-4-yl)-6-nitro-1H-inden-1-one

The nitro derivative of 2-ethyl-2,3-dihydro-2-(1H-imidazol-4-yl)-1H-inden- 1-one (Karjalainen, A. J. et. al. U.S. Pat. No. 4,689,339) was prepared in the way described in Example 1. The yield was 100%. Mp. of the hydrochloride salt of the product was 226°–228° C.

MS: 271 (33, M$^+$), 256 (12, M-CH$_3$), 242 (100, M-CH$_2$CH$_3$), 196 (32, 242-NO$_2$)

The hydrochloride salt, $^1$H NMR (300 MHz, CD$_3$OD): δ0.87 (3H, t, J 7 Hz, CH$_2$CH$_3$), 1.96–2.20 (2H, m, CH$_2$CH$_3$), 3.66 and 3.78 (2H, AB q, J$_{AB}$ 19 Hz, the indan ring H$_2$-3), 7.65 (1H, d, J 1 Hz, im-5), 7.91 (1H, d, $^3$J 9 Hz, H-4), 8.50 (1H, d, $^4$J 2 Hz, H-7), 8.58 (1H, dd, $^3$J 9 1 Hz, $^4$J 2 Hz, H-5), 8.98 (1H, J 1 Hz, im-2)

6-Amino-2-ethyl-2,3-dihydro-2-(1H-imidazol-4-yl)-1H-inden-1-one

To 7.20 g (0.0265 mol) of 2-ethyl-2,3-dihydro-2-(1H-imidazol-4-yl)- 6-nitro-1H-inden-1-one dissolved in 70 ml of ethanol was added 0.7 g of 10% palladium on carbon and the mixture was shaken in an atmosphere of hydrogen at the room temperature. When the reduction came to a standstill the catalyst was removed. The filtrate was concentrated to give 6-amino-2-ethyl-2,3-dihydro-2-(1H-imidazol-4-yl)-1H-inden-1-one (5.96 g, 93%). The product was purified by flash chromatography eluting with methylene chloride—methanol mixture (9.5:0.5).

MS: 241 (36%, M$^+$), 212 (100%, M-CH$_2$CH$_3$)

Base, $^1$H NMR (300 MHz, CDCl$_3$): δ0.81 (3H, t, J 7 Hz, CH$_2$CH$_3$), 1.84–2.04 (2H, m, CH$_2$CH$_3$), 3.20 and 3.55 (2H, AB q, J$_{AB}$ 17 Hz, the indan ring H$_2$-3), 6.92 (1H, s, im-5), about 6.9 (1H, m, H-5), 6.97 (1H, s, H-7), 7.25 (1H, d, $^3$J 10 Hz, H-4), 7.51 (1H, s, im-2)

Base, $^{13}$C NMR (CD$_3$OD): δ9.42 (q), 31.85 (t), 38.88 (t), 55.15 (s), 108.77 (d), 117.39 (d), 125.28 (d), 127.90 (d), 136.48 (d), 137.67 (s), 140.37 (s), 144.48 (s), 149.07 (s), 188.78 (s)

2-Ethyl-6-fluoro-2,3-dihydro-2-(1H-imidazol-4-yl)-1H-inden-1-one

2-Ethyl-6-fluoro-2,3-dihydro-2-(1H-imidazol-4-yl)-1H-inden-1-one was prepared in the way described in Example 1. The product was purified by flash chromatography (the eluent methylene chloride methanol 9.5:0.5). Yield after purification was 75%. The hydrochloride salt of the product was prepared in ethyl acetate; mp. 167°–168° C.

MS: 244 (27, M$^3$), 215 (100, M-CH$_2$CH$_3$), 187 (10), 149 (14), 133 (18), 107 (12), 85 (14), 71 (12), 69 (10), 57 (24)

The hydrochloride salt, $^1$H NMR (300 MHz, CD$_3$OD): δ0.85 (3H, t, J 7 Hz, CH$_2$CH$_3$), 1.93–2.20 (2H, m, CH$_2$CH$_3$), 3.48 and 3.60 (2H, AB q J$_{AB}$ 17 Hz, the indan ring H$_2$-3), 7.43 (1H, dd, $^3$J$_{HF}$ 8 Hz, $^4$J$_{HH}$ 3 Hz, H-7), 7.53 (1H, m, $^4$J$_{HH}$ 3 Hz, H-5), 7.59 (1H, d, J 1 Hz, im-5), 7.68 (1H, dd, $^3$J$_{HH}$ 8 Hz, $^4$J$_{HF}$ 5 Hz, H-4), 8.93 (1H, d, J 1 Hz, im-2)

The hydrochloride salt, $^{13}$C NMR (CD$_3$OD): δ9.32 (CH$_2$CH$_3$), 32.35 (CH$_2$CH$_3$), 37.91 (C-3), 54.18 (C-2), 110.89 ($^2$J$_{CCF}$ 22 Hz, C-7), 117.83 (im-5), 124.83 ($^2$J$_{CCF}$ 24 Hz, C-5), 129.97 ($^3$J$_{CCCF}$ 8 Hz, C-4), 135.38 (im-4), 136.24

(im-2), 137.30 ($^3J_{CCCF}$ 7 Hz, C-7a), 149.57 ($^4J_{CCCCF}$ 2 Hz, C-3a), 164.12 ($J_{CF}$ 248 Hz, C-6), 193.93 (C=O).

EXAMPLE 5

6-FLUORO-2,3-DIHYDRO-2-(1H-IMIDAZOL-4-YL)-2-METHYL-1H-INDEN-1-ONE

6-Fluoro-2,3-dihydro-2-(1H-imidazol-4-yl)-2-methyl-1H-inden-1-one and its intermediates were synthesized from 2,3-dihydro-2-(1H-imidazol- 4-yl)-2-methyl-1H-inden-1-one (Karjalainen, A. J. et. al. U.S. Pat. No. 4,689,339) according to the procedure used in Example 4.

2,3-Dihydro-2-(1H-imidazol-4-yl)-2-methyl-6-nitro-1H-inden-1-one

MS: 257 (100, M$^+$), 242 (98, M-CH$_3$), 228 (65)

Base, $^1$H NMR (300 MHz, CDCl$_3$+CD$_3$OD): δ1.62 (3H, s, CH$_3$), 3.32 and 3.94 (2H, AB q, J$_{AB}$ 18 Hz, H$_2$-3), 6.96 (1H, s, im-5), 7.52 (1H, s, im- 2), 7.70 (1H, d, J 9 Hz, H-5), 8.51 (1H, dd, $^3$J 9 Hz, $^4$J 2 Hz, H-5), 8.60 (1H, d, J 2 Hz, H-7)

6-Amino-2,3-dihydro-2-(1H-imidazol-4-yl)-2-methyl-1H-inden-1-one

MS: 227 (100, M$^3$ ), 212 (85, M-CH$_3$), 198 (50)

Base, $^1$H NMR (300 MHz, CD$_3$OD): δ1.52 (3H, s), 3.07 and 3.52 (2H, AB q, J$_{AB}$ 17 Hz, H$_2$-3), 6.93 (1H, s, im-5), 6.98 (1H, d, J 2 Hz, H-7), 7.03 (1H, dd, $^3$J 8 Hz, $^4$J 2 Hz, H-5), 7.27 (1H, d, J 8 Hz, H-4), 7.55 (1 H, s, im-2)

6-Fluoro-2,3-dihydro-2-(1H-imidazol-4-yl)-2-methyl-1H-inden-1-one

The hydrochloride salt: Mp. 164°–167° C.

MS: 230 (100, M$^+$), 215 (95, M-CH$_3$), 201 (80), 187 (25), 174 (25), 133 (25)

The hydrochloride salt, $^1$H NMR (300 MHz, CD$_3$OD): δ1.65 (3H, s, CH$_3$), 3.38 and 3.65 (2H, AB q, J$_{AB}$ 17 Hz, H$_2$-3), 7.45–7.66 (3H, m, H-4, H-5, H-7), 7.54 (1H, s, im-5), 8.85 (1H, s, im-2)

EXAMPLE 6

6CHLORO-2-ETHYL-2,3-DIHYDRO-2-(1H-IMIDAZOL-4-YL)-1H-INDEN-1-ONE

In the flask were placed 2.95 g (0.0122 mol) of 6-amino-2-ethyl-2,3-dihydro- 2-(1H-imidazol-4-yl)-1H-inden-1one, 4.5 ml of water and 4.5 ml of concentrated hydrochloric acid. This solution was cooled to 0° C. and a solution of 0.84 g (0.0122 mol) of sodium nitrite in 3 ml of water was run in slowly while the temperature was kept below 5° C. After the addition the mixture was stirred for one hour at 0° C.

In another flask 1.46 g (0.0147 mol) of copper(I) chloride was dissolved in the mixture of water (6 ml) and concentrated hydrochloric acid (4.5 ml) and the solution was chilled in an ice-water bath.

The ice-cold diazonium solution was added, with stirring, to the copper(I) chloride solution while the temperature was kept at 0° C. After the addition the stirring was continued for thirty minutes at 0° C. The temperature was then let to increase slowly to the room temperature. After this the mixture was heated for 1.5 hours at 70° C.

After the mixture was cooled, water was added and the solution was made alkaline. The product was extracted into ethyl acetate, washed with water and evaporated. The crude product was purified by flash chromatography (the eluent methyl chloride—methanol (9.5:0.5). The hydrochloride salt of 6-chloro-2-ethyl-2,3-dihydro-2-(1H-imidazol-4-yl)-1H-inden-1-one was prepared in ethyl acetate; mp. 198°–201° C.

MS: 260 and 262 (22 and 8, M$^+$), 231 and 233 (100 and 34, M-CH$_2$CH$_3$)

The hydrochloride salt, $^1$H NMR (300 MHz, CD$_3$OD): δ0.84 (3H, t, J 7 Hz, CH$_2$CH$_3$), 1.93–2.19 (2H, m, CH$_2$CH$_3$), 3.48 and 3.60 (2H, AB q, J$_{AB}$ 18 Hz, the indan ring H$_2$-3), 7.57 (1H, d, J 1 Hz, im-5), 7.64 (1H, distorted d, J 8 Hz, H-4), 7.73 (1H, s, H-7), 7.74 (1H, distorted d, H-5), 8.90 (1H, s, im-2)

EXAMPLE 7

4-(5-FLUORO-2,3-DIHYDRO-1H-INDEN-2-YL)-1H-IMIDAZOLE

4(2,3-Dihydro-5-nitro-1H-inden-2-yl)-1H-imidazole

Concentrated sulphuric acid (11 ml) was cooled to –10° C. and the mixture of 4-(2,3-dihydro-1H-inden-2-yl)-1H-imidazole hydrochloride (Karjalainen, A. J. et. al. U.S. Pat. No. 4,689,339; 2.70 g, 0.0122 mol) and ureanitrate (1.50 g, 0.0122 mol) was added in small portions to the acid solution at –10° C. After the reaction the solution was poured onto ice. The solution was made alkaline and extracted three times with ethyl acetate. The organic extracts were combined, dried and evaporated to dryness. The yield 1.28 g, 91%.

MS: 229 (100, M$^+$), 228 (55, M-H), 214 (19), 212 (26), 201 (12), 183 (16, M-NO$_2$), 182 (61, 228-NO$_2$), 168 (14), 153 (13), 154 (16), 129 (10), 128 (18), 127 (16), 115 (16), 91 (12%), 77 (12), 68 (19)

Base, $^1$H NMR (300 MHz, CDCl$_3$+one drop of CD$_3$OD): δ3.18 (2H, dd, J$_{gem}$ 16 Hz, J$_{vis}$ 8 Hz, the indan ring one H-1 and one H-3), 3.39 (2H, dd, J$_{gem}$ 16 Hz, J$_{vis}$ 8 Hz, the indan ring another H-1 and another H-3), 3.80 (1H, quintet, J$_{vis}$ 8 Hz, the indan ring H-2), 6.80 (1H, s, im-5), 7.34 (1H, d, J 8 Hz, H-7), 7.57 (1H, s, im-2), 8.05 (1H, d, J 8 Hz, H-6), 8.06 (1H, s, H-4)

4-(5-Amino-2,3-dihydro-1H-inden-2-yl)-1H-imidazole

Reduction of 4-(2,3-dihydro-5-nitro-1H-inden-2-yl)-1H-imidazole to 4-(5-amino-2,3-dihydro=1H-inden-2-yl)-1H-imidazole was carried out in the way described in Example 4. Yield was 94%. Purification of the product was performed by flash chromatography (the eluent methylene chloride—methanol 9.5:0.5).

MS: 199 (100, M$^+$), 198 (34, M-H), 184 (32), 171 (12), 157 (12), 149 (21), 131 (21), 130 (25), 99 (14), 98 (14), 77 (10), 69 (18)

Base, $^1$H NMR (300 MHz, CD$_3$OD): δ2.85–2.96 (2H, m, one H-1 and one H-3), 3.09–3.18 (2H, m, another H-1 and another H-3), 3.57 (1H, quintet, J 8 Hz, H-2), 6.54 (1H, dd, $^3$J 8 Hz, $^4$J 2 Hz, H-6), 6.63 (1H, s, H-4), 6.78 (1H, s, im-5), 6.93 (1H, d, J 8 Hz, H-7), 7.57 (1H, s, im-2)

4-(5-Fluoro-2,3-dihydro-1H-inden-2-yl)-1H-imidazole 4-(5-Fluoro-2,3-dihydro-1H-inden-2-yl)-1H-imidazole was prepared from 4-(5-amino-2,3-dihydro-1H-inden-2-yl)-1H-imidazole in the way described in Example 1. The yield of the crude product was 99%. The product was purified by flash chromatography (the eluent methylene chloride—methanol 9.5:0.5). The hydrochloride salt of the product was prepared in ethyl acetate: mp. 189°–191° C.

MS: 202 (100, M$^+$), 201 (64, M-H), 187 (51), 174 (25), 160 (16), 147 (14), 146 (17), 133 (32), 132 (16), 100 (10)

The hydrochloride salt, $^1$H NMR (300 MHz, CD$_3$OD): δ3.01–3.14 (2H, m, one H-1 and one H-3), 3.34–3.45 (2H, m, another H-1 and another H-3), 3.84 (1H, quintet, J 8 Hz, H-2), 6.90 (1H, m, H-6), 6.99 (1H, d, $^3J_{HF}$ 9 Hz, H-4), 7.24 (1H, dd, $^3J_{HH}$ 8 Hz, $^4J_{HF}$ 5 Hz, H-7), 7.37 (1H, s, im-5), 8.83 (1H, s, im-2)

The hydrochloride salt, $^{13}$C NMR (CD$_3$OD): δ37.37 (C-2), 38.94 (C-1), 39.75 ($^4J_{CCCCF}$ 2 Hz, C-3), 112.42 ($^2J_{CCF}$ 23 Hz, C-4), 114.65 ($^2J_{CCF}$ 23 Hz, C-6), 116.18 (im-5), 126.63 ($^3J_{CCCF}$ 9 Hz, C-7), 135.15 (im-2), 138.27 ($^4J_{CCCCF}$ 2 Hz, C-7a), 138.47 (im-4), 145.05 ($^3J_{CCCF}$ 8 Hz, C-3a), 163.80 ($^2J_{CF}$ 242 Hz, C-5)

EXAMPLE 8

4-(4-FLUORO-2,3-DIHYDRO-1H-INDEN-2-YL)-1H-IMIDAZOLE 4-(4-Amino-2,3-dihydro-1H-inden-2-yl)-1H-imidazole In the nitration of 4-(2,3-dihydro-1H-inden-2-yl)-1H-imidazole (Example 7) also a small amount of 4-(2,3-dihydro-4-nitro-1H-inden-2-yl)-1H-imidazole was formed. After the catalytic hydrogenation the 4-amino isomer was isolated and purified by flash chromatography.

MS: 199 (100, M$^+$), 198 (40, M-H), 184 (29), 183 (13), 171 (10), 149 (10), 131 (20), 130 (28), 69 (20)

4-(4-Fluoro-2,3-dihydro-1H-inden-2-yl)-1H-imidazole 4-(4-Fluoro-2,3-dihydro-1H-inden-2-yl)-1H-imidazole was prepared according to the fluorination method of Example 1. The product was purified by flash chromatography (the eluent methylene chloride methanol 9.5:0.5). The hydrochloride salt of the product was prepared in ethyl acetate; mp. 180°–183° C.

MS: 202 (100, M$^+$), 201 (72, M-H), 187 (38), 174 (24), 160 (12), 147 (12), 146 (16), 134 (15), 133 (27), 100 (11), 68 (12)

The hydrochloride salt, $^1$H NMR (300 MHz, CD$_3$OD): δ3.04–3.18 (2H, m one, H-1 and one H-3), 3.36–3.53 (2H, m, another H-1 and another H-3), 3.86 (1H, quintet, J 8 Hz, H-2), 6.91 (1H, t, $^3J_{HH}$ 9 Hz, H-6), 7.09 (1H, d, $^3J_{HH}$ 9 Hz, H-7), 7.18–7.25 (1H, m, H-5), 7.39 (1H, s, im-5), 8.83 (1H, s, im-2)

EXAMPLE 9

4-(2-ETHYL-5,6-DIFLUORO-2,3-DIHYDRO-1H-INDEN-2-YL)-1H-IMIDAZOLE 4-(2-Ethyl-5-fluoro-2,3-dihydro-6-nitro-1H-inden-2-yl)-1H-imidazole 4-(2-Ethyl-5-fluoro-2,3-dihydro=-1H-inden-2-yl)-1H-imidazole (4.56 g, 0.0198 mol) was added to 24 ml of concentrated sulphuric acid at −10° C. Ureanitrate (2.44 g, 0.0198 mol) was added in small portions at −10° C. After the reaction the solution was poured onto ice. The solution was made alkaline and extracted with ethyl acetate. The organic extracts were dried and evaporated to dryness.

MS: 275 (21, M$^+$), 246 (100, M-CH$_2$CH$_3$), 200 (34, 246-NO$_2$), 199 (11)

Base, $^1$H NMR (300 MHz, CDCl$_3$): δ0.77 (3H, t, J 7 Hz, CH$_2$CH$_3$), 1.90 (2H, q, J 7 Hz, CH$_2$CH$_3$), 3.08 and 3.32 (2H, AB q, $J_{AB}$ 16 Hz, H$_2$-1 or H$_2$-3), 3.11 and 3.38 (2H, AB q, $J_{AB}$ 17 Hz, H$_2$-1 or H$_2$-3), 6.76 (1H, s, im-5), 7.07 (1H, d, $^3J_{HF}$ 11 Hz, H-4), 7.62 (1H, s, im-2), 7.84 (1H, d, $^4J_{HF}$ 7 Hz, H-7)

4-(5-Amino-2-ethyl-6-fluoro-2,3-dihydro-1H-inden-2-yl)-1H-imidazole 4-(2-Ethyl-5-fluoro-2,3-dihydro-6-nitro-1H-inden-2-yl)-1H-imidazole was hydrogenated to 4-(5-amino-2-ethyl-6-fluoro-2,3-dihydro-1H-inden-2-yl)-1H-imidazole in the way described in Example 4. The yield of the crude product was 85%. Purification was performed by flash chromatography (the eluent methylene chloride—methanol 9.5:0.5).

MS: 245 (49, M$^+$), 230 (12, M-CH$_3$), 216 (100, M-CH$_2$CH$_3$), 148 (20), 107 (18)

Base, $^1$H NMR (300 MHz, CDCl$_3$): δ0.73 (3H, t, J 7 Hz, CH$_2$CH$_3$), 1.83 (2H, q, J 7 Hz, CH$_2$CH$_3$), 2.90 and 3.10 (2H, AB q, $J_{AB}$ 16 Hz, H$_2$-1 or H$_2$-3), 2.92 and 3.11 (2H, AB q, $J_{AB}$ 15 Hz, H$_2$-1 or H$_2$-3), 6.56 (1H, d, $^4J_{HF}$ 9 Hz, H-4), 6.71 (1H, s, im-5), 6.76 (1H, d, $^3J_{HF}$ 11 Hz, H-7), 7.48 (1H, s, im-2)

4-(2-Ethyl-5,6-difluoro-2,3-dihydro-1H-inden-2-yl)-1H-imidazole

Fluorination of 4-(5-amino-2-ethyl-6-fluoro-2,3-dihydro-1H-inden-2-yl)-1H-imidazole was performed in the way described in Example 1.

MS: 248 (16, M$^+$), 219 (100, M$^+$)

The hydrochloride salt, $^1$H NMR (300 MHz, CD$_3$OD): δ0.80 (3H, t, J 7 Hz, CH$_2$CH$_3$), 1.93 (2H, q, J 7 Hz, CH$_2$CH$_3$), 3.16 and 3.25 (4H, AB q, $J_{AB}$ 16 Hz, H$_2$-1 and H$_2$-3), 7.12 (2H, dd, $^3J_{HF}$=$^4J_{HF}$ 9 Hz, H-4 and H-7), 7.39 (1H, d, J 1 Hz, im-5), 8.87 (1H, d, J 1 Hz, im-2)

EXAMPLE 10

4-(5,6-DICHLORO-2-ETHYL-2,3-DIHYDRO-1H-INDEN-2-YL)-1H-IMIDAZOLE 4-(5-chloro-2-ethyl-2,3-dihydro-1H-inden-2-yl)-1H-imidazole was prepared through diazotization of 4-(5-amino-2-ethyl-2,3-dihydro-1H-inden-2-yl)-1H-imidazole in the way described in example 6. The procedure of example 9 was used for the synthesis of the nitro and amino derivatives of 4-(5-chloro-2-ethyl-2,3-dihydro-1H-inden-2-yl)-1H-imidazole. Chlorination was carried out as described in example 6

4-(5-chloro-2-ethyl-2,3-dihydro-1H-inden-2-yl)-1H-imidazole

The hydrochloride salt: Mp. 147°–149° C.

MS: 246/248 (28/9. M+), 217/219 (100/33), 183 (11), 182 (16), 181 (19)

The hydrochloride salt, $^1$H NMR (300 MHz, CD$_3$OD): δ0.80 (3H, t, J 7 Hz, CH$_2$CH$_3$), 1.93 (2H, q, J 7 Hz, CH$_2$CH$_3$), 3.16 and 3.25 (2H, AB q, $J_{AB}$= 16 Hz, the indan ring H$_2$-1 or H$_2$-3), 3.18 and 3.28 (2H, AB q, J$_{AB}$=16 Hz, the indan ring H$_2$-1 or H$_2$-3), 7.12–7.23 (3H, m, H-4, H-6, H-7), 7.38 (1H, d, J 1 Hz, im-5), 8.87 (1H, d, J 1 Hz, im-2)

4-(5-chloro-2-ethyl-2,3-dihydro-6-nitro-1H-inden-2-yl)-1H-imidazole

MS: 291/293 (22/7, M+), 262/264 (100/33), 216/218 (28/9), 181 (10)

Base, $^1$H NMR (300 MHz, CDCl$_3$+CD$_3$OD): δ0.74 (3H, t, J 7 Hz, CH$_2$CH$_3$), 1.87 (2H, q, J 7 Hz, CH$_2$CH$_3$), 3.08 and 3.29 (2H, AB q, J 16 Hz, the indan ring H$_2$-1 or H$_2$-3), 3.09 and 3.32 (2H AB q, J 17 Hz, the indan ring H$_2$-1 or H$_2$-3), 6.72 (1H, s, im-5), 7.34 (1H, s, H-4), 7.56 (1H, s, im-2), 7.69 (1H, s, H-7)

4-(5-amino-6-chloro-2-ethyl-2,3-dihydro-1H-inden-2-yl)-1H-imidazole

MS: 261/263 (60/24, M+), 232/234 (100/35), 196 (53)

Base, $^1$H NMR: (300 MHz, CD$_3$OD): δ0.71 (3H, t, J 7 Hz, CH$_2$CH$_3$), 1.81 (2H, q, J 7 Hz, CH$_2$CH$_3$), 2.91 and 3.10 (4H, AB q, J 15 Hz the indan ring H$_2$-1 and H$_2$-3), 6.68 (1H, s, H-4), 6.76 (1H, d, J 1 Hz, im-5), 6.99 (1H, s, H-7), 7.61 (1H, J 1 Hz, im-2)

4-(5,6-dichloro-2-ethyl-2,3-dihydro-1H-inden-2-yl)-1H-imidazole

MS: 280/282/284 (22/14/2, M+), 251/253/255 (100/64/11)

Base, $^1$H NMR (300 MHz, CD$_3$OD): δ0.72 (3H, t, J 7 Hz, CH$_2$CH$_3$), 1.84 (q, 2H, J 7 Hz, CH$_2$CH$_3$), 2.99 and 3.21 (4H, AB, q, J 16 Hz, the indan ring H$_2$-1 and H$_2$-3), 6.80 (1H, s, im-5), 7.26 (2H, s, ArH), 7.61 (1H, s, im-2)

EXAMPLE 11

4-(5-CHLORO-2-ETHYL-6-FLUORO-2,3-DIHYDRO-1H-INDEN-2-YL)-1H-IMIDAZOLE

Chlorination of 4-(5-amino-2-ethyl-6-fluoro-2,3-dihydro-1H-inden-2-yl)- 1H-imidazole (of example 9) was carried out as described in example 6.

MS: 264/266 (34/11, M+), 235/237 (100/35)

Base, $^1$H NMR (300 MHz, CD$_3$OD): δ0.72 (3H, t, J 7 Hz, CH$_2$CH$_3$), 1.85 (2H, q, J 7 Hz, CH$_2$CH$_3$), 3.00 and 3.20 (2H, AB q, J 16 Hz, the indan ring H$_2$-1 or H$_2$-3), 3.02 and 3.22 (2H, AB q, J 16 Hz, the indan ring H$_2$-1 or H$_2$-3), 6.80 (1H, s, im-5), 7.02 (1H, d, $^3$J$_{HF}$ 9 Hz, H-4), 7.22 (1H, d, $^4$J$_{HF}$ 7 Hz, H-7), 7.62 (1H, s, im-2)

We claim:

1. A substituted imidazole according to the formula

I wherein

Y is —CH$_2$— or —CO—;

R$_1$ is F, Cl or OH;

R$_2$ is H, F or Cl; and

R$_3$ is H, CH$_3$ or CH$_2$CH$_3$, excluding 4-(5-chloro-2,3-dihydro-1H-inden- 2-yl)-1H-imidazole and 4-(4-chloro-2,3-dihydro-1H-inden-2-yl)- 1H-imidazole; or a pharmaceutically acceptable salt thereof.

2. A compound according to claim 1 where R$_1$ is F and R$_2$ is H or F.

3. A compound according to claim 2, where R$_2$ is H.

4. A compound according to claim 1, wherein R$_3$ is hydrogen or CH$_2$CH$_3$.

5. A compound according to claim 1, wherein Y is —CH$_2$—.

6. A compound according to claim 1, wherein the compound is 4-(2-Ethyl-5-fluoro-2,3-dihydro-1H-inden-2-yl)-1-imidazole or its pharamaceutically acceptable non-toxic salt.

7. A compound according to claim 1, wherein the compound is 4-(5-Fluoro-2,3-dihydro-2-methyl-1H-inden-2-yl)-1H-imidazole or its pharmaceutically acceptable non-toxic salt.

8. A compound according to claim 1, wherein the compound is 4-(2-Ethyl-5,6-difluoro-2,3-dihydro-1H-inden-2-yl)-1H-imidazole or its pharmaceutically acceptable non-toxic salt.

9. A compound according to claim 1, wherein the compound is 2-Ethyl-6-fluoro-2,3-dihydro-2-(1H-imidazol-4-yl)-1H-inden-1-one or its pharmaceutically acceptable non-toxic salt.

10. A compound according to claim 1, wherein the compound is 6-Chloro-2-ethyl-2,3-dihydro-2-(1H-imidazol-4-yl)-1H-inden-1-one or its pharmaceutically acceptable non-toxic salt.

11. A compound according to claim 1, wherein the compound is 4-(4-Fluoro-2,3-dihydro-1H-inden-2-yl)-1H-imidazole or its pharmaceutically acceptable non-toxic salt.

12. A compound according to claim 1, wherein the compound is 4-(5-Fluoro-2,3-dihydro-1H-inden-2-yl)-1H-imidazole or its pharmaceutically acceptable non-toxic salt.

13. A compound according to claim 1, wherein the compound is 2-Ethyl-2-(1H-imidazol-4-yl)-5-indanol or its pharmaceutically acceptable non-toxic salt.

14. A compound according to claim 1, wherein the compound is 4-(5,6-dichloro-2-ethyl-2,3-dihydro-1H-inden-2-yl)-1H-imidazole or its pharmaceutically acceptable non-toxic salt.

15. A compound according to claim 1, wherein the compound is 4-(5-chloro-2-ethyl-2,3-dihydro-1H-inden-2-yl)-1H-imidazole or its pharmaceutically acceptable non-toxic salt.

16. A method for the preparation of a compound according to the formula I

I wherein

Y is —CH$_2$—;

R$_1$ is F or Cl;

R$_2$ is H and

R$_3$ is H, CH$_3$ or CH$_2$CH$_3$;

comprising nitrating a compound of formula (II)

where $R_3$ is as defined above to give the compounds of formulae (III) and (IV)

reducing the compounds of formula (III) and formula (IV) to the corresponding amino substituted compounds of formulae (V) and (VI)

converting the amino substituted compounds of formula (V) and formula (VI) to their corresponding diazonium salts and replacing the diazonium groups with halogen to yield the compounds of formulae (VII) and (VIII)

where X is F or Cl.

17. A method according to claim 16, in the formulae VII and VIII X is F.

18. A method according to claim 17, said diazonium salts are generated by reacting the amine of formula V and/or VI with mineralic acid on sodium nitrite at lowered temperature.

19. A method according to claim 16, in the formula VII and VIII X is Cl.

20. A method according to claim 19, the said diazonium salts are formed by reacting the amine of formula V and/or VI with hydrochloric acid and sodium nitrite at lowered temperature.

21. A method for the preparation of the compound according to the formula wherein
Y is —CH$_2$—;
X is F or Cl;
X$_2$ is F or Cl and R$_3$ is H, CH$_3$ or CH$_2$CH$_3$;
comprising nitrating a compound of formula VII wherein X is F or Cl and R$_3$ is the same as defined above to give a compound of formula IX reducing the nitro group to the corresponding amino group;

converting the amino group to a diazonium group and converting the diazonium group to halogen.

22. A method for the preparation of the compound according to formula X wherein
X is F or Cl and R$_3$ is H, CH$_3$ or CH$_2$CH$_3$,
comprising nitrating a compound of formula XI where $R_3$ is the same as defined above to give a compound of formula XI' reducing the nitro group of the compound of formula (XI') to an amino group to give a compound of the formula (XI")

converting the amino group of the compound of formula (XI") to a diazonium group and thereafter converting the diazonium group to halogen.

23. A method for the preparation of the compound according to formula (XX)

wherein
$X_1$ is F or Cl,
$X_2$ is F or Cl and
$R_3$ is H, $CH_3$ or $CH_2CH_3$,
comprising nitrating a compound of formula (XX')

wherein $X_1$ and $R_3$ are the same as defined above to give the compound of formula (XX")

reducing the nitro group to an amino group to give a compound of the formula (XX''')

converting the amino group of the compound of formula (XX''') to a diazonium group and converting the diazonium group to halogen.

24. A method for the preparation of a compound according to the formula XII where $R_3$ is H, $CH_3$ or $CH_2CH_3$;

comprising reacting a compound of the formula V where $R_3$ is the same as given above, with sodium nitrite in the presence of concentrated sulfuric acid to give a diazonium salt and decomposing the diazonium salt thus obtained to yield the compound of formula (XII).

25. A method of treatment of cognitive disorders comprising administering to a subject an effective amount of a substituted imidazole according to the formula wherein
Y is —$CH_2$— or —CO—
$R_1$ is F, Cl or OH;
$R_2$ is H, F or Cl; and
$R_3$ is H, or a pharmaceutically acceptable salt thereof.

* * * * *